United States Patent [19]

Beckers et al.

[11] 3,935,287

[45] Jan. 27, 1976

[54] STABILIZED METHYL CHLOROFORM

[75] Inventors: Norman L. Beckers, Chardon; Edward A. Rowe, Mentor, both of Ohio

[73] Assignee: Diamond Shamrock Corporation, Cleveland, Ohio

[22] Filed: Oct. 25, 1974

[21] Appl. No.: 517,941

Related U.S. Application Data

[60] Division of Ser. No. 243,072, April 11, 1972, Pat. No. 3,864,413, which is a continuation-in-part of Ser. No. 5,101, Jan. 22, 1970, abandoned.

[52] U.S. Cl............................................ 260/652.5 R
[51] Int. Cl.².......................................... C07C 17/40
[58] Field of Search ............................ 260/652.5 R

[56] References Cited

UNITED STATES PATENTS

| | | | |
|---|---|---|---|
| 3,189,552 | 6/1965 | Sims............................. | 260/652.5 R |
| 3,201,482 | 8/1965 | Fredenburg.................. | 260/652.5 R |
| 3,549,715 | 12/1970 | Cormany et al. ............ | 260/652.5 R |
| 3,564,061 | 2/1971 | Correia et al................ | 260/652.5 R |

*Primary Examiner*—D. Horwitz
*Attorney, Agent, or Firm*—William A. Skinner

[57] ABSTRACT

The tendency for methyl chloroform to decompose in the presence of metals, particularly aluminum, is inhibited by a stabilizer mixture comprising an epoxide, a nitroalkane, trioxane and either propylene glycol mono-methyl ether, dioxepane or a mixture thereof.

3 Claims, No Drawings

STABILIZED METHYL CHLOROFORM

REFERENCE TO A CO-PENDING APPLICATION

This is a division of application Ser. No. 243,072 filed Apr. 11, 1972, now U.S. Pat. No. 3,864,413, which is in turn a continuation-in-part of application Ser. No. 5,101 filed Jan. 22, 1970, and now abandoned.

BACKGROUND OF THE INVENTION

The usefulness of various chlorinated lower aliphatic hydrocarbons, particularly for the liquid and/or vapor phase degreasing of metals, is by now well known. Besides their excellent cleaning properties, these chlorinated solvents are well suited for industrial use owing to their lack of flammability and relatively low cost. The most widely used of these solvents are carbon tetrachloride, trichloroethylene, perchloroethylene and methyl chloroform (1,1,1-trichloroethane). Of particular interest from this group is methyl chloroform, the excellent solvency and low toxicity of which make it particularly suitable for the industrial cleaning (degreasing) of metals.

A problem in the commercialization of methyl chloroform has arisen, however, owing to its pronounced tendency to decompose in the presence of a number of metals, especially aluminum. Thus, while others of the chlorinated solvents, such as perchloroethylene, must be stabilized against decomposition induced by a wide variety of factors, the problem is nowhere near as marked as in the case of methyl chloroform, which, if exposed unprotected to aluminum, will be rendered useless within a matter of minutes.

Thus it will be apparent, and indeed research has shown, that while other chlorinated solvents may be stabilized through the use of small quantities of a wide variety of substances, the compounds capable of stabilizing methyl chloroform against metal-induced decomposition are quite limited in number and generally must be used in comparatively large amounts. Obviously, the requirements being strict and the selection limited, a number of problems have arisen in attempting to perfect a stabilizer system which will protect methyl chloroform and the metals being treated therewith against decomposition in both the liquid and vapor phases in the presence of a wide variety of contaminants. First, relatively large quantities being required, the stabilizers must be economically practical. Further, while the problems of liquid phase stabilization are often different from those of vapor phase stabilization and hence different stabilizers will be useful, the methyl chloroform may be used interchangeably for both liquid and vapor degreasing applications and therefore the components must be compatible over a wide range of temperatures.

While generalizations are indeed difficult with respect to the stabilization of methyl chloroform, it may be safely stated that many of the stabilizer systems used commercially and set forth in the patent literature describe and feature the use of nitroalkanes and epoxides. Although it is true that many stabilizer systems are "built" from this nitroalkane-epoxide base, the combination itself is not always completely effective for the stabilization of methyl chloroform and it is the selection of the remaining components of any system which determines its ultimate success or failure.

STATEMENT OF THE INVENTION

Therefore, it is an object of the present invention to provide a multi-component stabilizer system for the inhibition of the decomposition of methyl chloroform, particularly when used as a solvent for the liquid and vapor phase degreasing of metals.

It is a further object of the present invention to improve upon and make commercially practical a stabilizer system for methyl chloroform based upon a nitroalkane-epoxide combination.

These and further objects of the present invention will become apparent to those skilled in the art from the description and claims which follow.

It has now been found that a composition particularly suitable for metal degreasing applications comprises methyl chloroform together with a stabilizing amount of a mixture of 1) a nitroalkane, 2) an epoxide, 3) trioxane and 4) an additive compound selected from the group consisting of propylene glycol mono-methyl ether and dioxepane. The effectiveness of this composition is enhanced by the additional presence of an alcohol selected from the group consisting of methyl butynol and t-amyl alcohol, and, when such an alcohol is used, a hydrocarbon may be added with further beneficial effect. Optimum compositions for certain degreasing applications also include an alkaline compound. Such compositions and variations thereof are readily adaptable to the varied requirements of the metal degreasing field and may also be used in any other application where a stabilized grade of methyl chloroform is required.

DESCRIPTION OF THE PREFERRED EMBODIMENTS

The term "nitroalkane," as used in the specification and claims, is intended to refer to those nitro-aliphatic compounds generally used in the stabilization of chlorinated solvents, preferably those containing from 1–3 carbon atoms. Included are nitromethane, nitroethane, 1-nitropropane and 2-nitropropane.

The definition of the term "epoxide" is also that commonly used in the chlorinated solvents art and is intended to especially refer to aliphatic epoxides substituted or unsubstituted, containing from 3–8 carbon atoms. A primary consideration is that the boiling point of the epoxide compound does not differ substantially from that of methyl chloroform. Illustrative of the preferred epoxides are butylene oxide, propylene oxide, epichlorohydrin and methyl glycidyl ether.

The term "hydrocarbon" refers to a wide variety of materials such as straight chain or cyclic aliphatics, both saturated and unsaturated, as well as aromatics. Examples of such hydrocarbons useful in the invention are; hexane, heptane, octane, hexene, trimethyl pentene, cyclopentane, cyclohexane, cyclohexene, cyclooctene, toluene and the like. Many other hydrocarbons will also be useful depending upon, primarily, their boiling points and economics, with a wider variety obviously being useful for cold degreasing applications.

The use of the term "alkaline compound" in referring to the optimum compositions of the present invention is intended to include both those compounds which are alkaline per se, e.g., amines, and so called alkaline precursors, e.g., oximes or hydrazones. The alkaline compounds useful are those soluble in methyl chloroform and generally have boiling points substantially corresponding to methyl chloroform. It is apparent, however, that certain of these alkaline compounds form azeotropes with the methyl chloroform and/or other components of the stabilizer system thus altering their apparent boiling points. Those alkaline compounds especially preferred at this time include N-methyl morpholine, diisopropylamine and pyrrolidine.

It should be understood that the term "dioxepane" is used in the generic sense to include both 1,3- and 1,4-dioxepane. The 1,3 isomer is most common and hence preferred. However, it may be "contaminated" with or replaced by the 1,4 material without evident change.

The apparent purpose of both trioxane and propylene glycol mono-methyl ether and/or dioxepane is to act as an extender for the nitroalkane-epoxide base. However, it has been found that trioxane, while effective and economically desirable, cannot be incorporated into methyl chloroform in sufficient amounts, owing to its tendency on boiling to concentrate in the sump and crystallize from solution, to be effective. Further additions of propylene glycol mono-methyl ether and/or dioxepane, however, provide the necessary stabilization to render the system both effective and practical. The invention is thus most useful in the usual instance where large amounts of stabilizers must be present.

While the combination of methyl chloroform with a nitroalkane, an epoxide, trioxane and an additive compound selected from the group consisting of propylene glycol mono-methyl ether and dioxepane is quite effective for most applications it has been found that the effectiveness of the stabilizer system, especially its ability to resist aluminum attack at ambient temperatures upon dilution, is improved by the addition of an alcohol selected from the group consisting of t-amyl alcohol and methyl butynol. This function is considered important since a commercial product should be able to withstand considerable dilution without any substantial loss in effectiveness. This requirement is met by either t-amyl alcohol, methyl butynol, or mixtures thereof, without the problem usually inherent in the use of most alcohols for the stabilization of methyl chloroform solutions when used for vapor phase degreasing. Particularly, this problem relates to the fact that, while several alcohols are found to be effective at ambient temperatures in cold degreasing applications, these alcohols often detrimentally affect steel or aluminum surfaces in contact therewith at reflux temperatures. The disclosed alcohols have been found to be uniquely effective.

The use of the alcohols just mentioned is rendered even more effective for dilution control, and the distillation range of the stabilized solvent is improved, by the additional presence of a hydrocarbon, for example, heptane. The economic advantage of such a relatively inexpensive material is readily apparent when it is realized that the presence of a hydrocarbon may allow a reduction in quantity of the other, more expensive, components.

Where the corrosion of steel in the presence of methyl chloroform in the vapor phase is a problem, it may be desirable to add one of the many alkaline compounds known to be useful for this purpose. One or more of these alkaline compounds may be added to the compositions of the present invention in the presence of the alcohol, a hydrocarbon, both or neither, as the requirements of the system dictate.

Generally the amount of the stabilizing mixture added to the methyl chloroform will be that required to effect stabilization, economically, over a wide range of conditions, which amount will vary according to the application. It is usually found, however, that the composition will include from 90–99 percent by weight of methyl chloroform and from 10–1 percent by weight of the stabilizer mixture. Preferably from 4–6 percent of the composition will consist of the stabilizing components.

Referring to the stabilizers themselves, they may be present in the total stabilized system in amounts, expressed in percents by weight, as follow: 0.1 to 2.0 nitroalkane; 0.05 to 0.5 epoxide; 0.1–1.0 trioxane; 0.1 to 2.0 propylene glycol mono-methyl ether and/or dioxepane; 0.1 to 2.0 t-amyl alcohol and/or methyl butynol; 0.1 to 2.0 hydrocarbon, and 0.001 to 0.1 alkaline compound.

In order that those skilled in the art may more readily understand and appreciate the present invention, the following specific examples are afforded. In these examples a number of tests are referred to and are used to evaluate the effectiveness of the various stabilizer systems.

The "aluminum scratch test" consists of immersing a section of aluminum metal in the methyl chloroform solution to be evaluated and scratching the immersed surface with a fine-pointed stylus in order to present a fresh surface to the solvent. The test, which is strictly qualitative in nature, is effective as a screening method since, obviously, if the stabilized methyl chloroform system cannot pass this simple test, it will not stand up to the more rigorous tests which follow. Evidence of failure is represented by "bleeding", i.e., continuous discoloration of the solvent, at the point of the scratch.

A further and more rigorous test applied to systems which pass the scratch test is the "72 hour aluminum reflux test". In this test 100 milliliters of the solvent system and 0.2 milliliter of water are placed in a flat-bottomed flask fitted with a condenser. Two strips of aluminum are inserted, one in the liquid in the flask (pot), the other hung in the condenser where the solvent vapor during the extended period of gentle reflux surrounds, condenses on, and drips from, the strip. Again the test is mainly qualitative in nature and poor results are readily evidenced by corrosion of the aluminum and discoloration of the solvent. A further use of this test is to determine the acid content of the stabilized solvent by measurement of the final pH. Unless otherwise stated, all systems have an initial pH of 7 or above. Upon completion of the 72 hour reflux test, the solvent is cooled and extracted in a 1:1 ratio with neutral water, the pH of the aqueous phase being subsequently determined. A low pH is of course indicative of the presence of acid liberated by the decomposition of the solvent and serves as an indication of the effectiveness of the stabilized system in preventing corrosion of the aluminum and decomposition of the solvent.

EXAMPLE 1

The Table, hereinbelow, compares the effectivness of the various multi-component compositions of the present invention and is for the most part self-explanatory.

TABLE

| Stabilizer System | | Total Wt. Stabilizers | A1* Scratch Test | 72 Hr. A1 Reflux Test | | |
|---|---|---|---|---|---|---|
| | | | | Pot** | Condenser** | pH |
| 1. | Nitroethane | 3.6% | | | | |
| | Butylene oxide | 0.4% | 4.0 | 3 | — | — | — |
| 2. | Propylene glycol mono-methyl ether (PGME) | 2.8% | 2.8 | 2 | — | — | — |
| 3. | Nitroethane | 0.8% | | | | | |
| | Butylene oxide | 0.4% | | | | | |
| | Trioxane | 2.8% | 4.0 | 1 | A*** | C | 4.5 |
| 4. | Nitroethane | 0.8% | | | | | |
| | Butylene oxide | 0.4% | | | | | |
| | PGME | 2.0% | | | | | |
| | Trioxane | 0.8% | 4.0 | 1 | A | C | 6.0 |
| 5. | Nitroethane | 0.8% | | | | | |
| | Butylene oxide | 0.4% | | | | | |
| | 1,3-Dioxepane | 1.8% | | | | | |
| | Trioxane | 1.0% | 4.0 | 1 | A | B/C | 4.4 |
| 6. | Nitroethane | 0.8% | | | | | |
| | Butylene oxide | 0.4% | | | | | |
| | 1,3-Dioxepane | 1.0% | | | | | |
| | PGME | 0.8% | | | | | |
| | Trioxane | 1.0% | 4.0 | 1 | A | B | 5.4 |
| 7. | Nitroethane | 0.8% | | | | | |
| | Butylene oxide | 0.4% | | | | | |
| | PGME | 2.0% | | | | | |
| | Trioxane | 0.8% | | | | | |
| | Methyl butynol | 1.0% | 5.0 | 1 | A | A | 6.7 |
| 8. | Nitroethane | 0.8% | | | | | |
| | Butylene oxide | 0.4% | | | | | |
| | PGME | 1.0% | | | | | |
| | Trioxane | 0.6% | | | | | |
| | t-Amyl alcohol | 1.5% | 4.3 | 1 | A | B | 7.0 |

Note:
*1 = no effect, 2 = pinholes but heals, 3 = continuous bleeding
**A = no corrosion, B = slight corrosion, C = severe corrosion
*** Trioxane crystals observed in pot on solvent loss.

It will be seen from the Table that the combination of nitroethane and butylene oxide (Sample 1) fails the scratch test and hence is unacceptable as a stabilizer system for methyl chloroform. PGME (Sample 2) also fails the scratch test. The addition of trioxane to Sample 1 (Sample 3) improves scratch test results but leaves an unacceptable residue on solvent loss simulating a vapor degreasing operation. However, as is shown by Samples 4, 5 and 6, the combination of nitroethane, butylene oxide, trioxane and PGME and/or dioxepane results in a stabilized methyl chloroform composition which is entirely suitable for use in cold degreasing applications as evidenced by the improved result on the aluminum scratch test and which leaves no unacceptable pot (sump) residue on distillation. Samples 7 and 8 show that the further addition of methyl butynol or t-amyl alcohol significantly improves the stabilized methyl chloroform system of Sample 4 to the effect that good to excellent results are obtained, under conditions simulating vapor degreasing applications, according to the 72 hour aluminum reflux test.

EXAMPLE 2

A methyl chloroform solution stabilized with 0.4% butylene oxide, 1.8% propylene glycol mono-methyl ether, 1.0% trioxane and 0.4% nitromethane gives excellent results on the aluminum scratch test. After the 72 hour aluminum reflux test, a final pH of 6.9 is obtained and the condenser strip is only slightly stained while the solvent remains water-white and clear.

EXAMPLE 3

A methyl chloroform solution stabilized with 0.4% butylene oxide, 1.0% propylene glycol mono-methyl ether, 0.5% trioxane, 1.5% t-amyl alcohol, 0.8% nitroethane, 1.5% heptane and 0.02% N-methyl morpholine gives excellent results on the aluminum scratch test. After the 72 hour aluminum reflux test, the condenser strip shows only a slight stain and the pH after the test is 7.6 while the solvent remains water-white and clear.

While the invention has been described with reference to certain specific and preferred embodiments thereof, it is not to be so limited since certain alterations may be made which are still within the scope of the appended claims.

What is claimed:

1. A stabilized composition which consists essentially of methyl chloroform containing
   a. 0.1 to 2.0 percent by weight of a nitroalkane of from 1 to 3 carbon atoms.
   b. 0.05 to 0.5 percent by weight of an aliphatic epoxide selected from the group consisting of propylene oxide, butylene oxide, epichlorohydrin and methyl glycidyl ether,
   c. 0.1 to 1.0 percent by weight of trioxane, and
   d. 0.1 to 2.0 percent by weight of propylene glycol monomethyl ether.
2. The composition of claim 1 wherein the nitroalkane is nitromethane and the aliphatic epoxide is butylene oxide.
3. The composition of claim 1 wherein the nitroalkane is nitroethane and the aliphatic epoxide is butylene oxide.

* * * * *